(12) United States Patent
Brady

(10) Patent No.: US 11,576,847 B2
(45) Date of Patent: Feb. 14, 2023

(54) COLOR COMPOSITION FORMULA AND METHOD

(71) Applicant: Shelly Kay Brady, Tulsa, OK (US)

(72) Inventor: Shelly Kay Brady, Tulsa, OK (US)

( * ) Notice: Subject to any disclaimer, the term of this patent is extended or adjusted under 35 U.S.C. 154(b) by 179 days.

(21) Appl. No.: 16/865,223

(22) Filed: May 1, 2020

(65) Prior Publication Data

US 2020/0345600 A1 Nov. 5, 2020

Related U.S. Application Data

(60) Provisional application No. 62/841,411, filed on May 1, 2019, provisional application No. 62/841,433, filed on May 1, 2019, provisional application No. 62/841,443, filed on May 1, 2019.

(51) Int. Cl.
| | | |
|---|---|---|
| *A61K 8/19* | (2006.01) |
| *A61Q 19/10* | (2006.01) |
| *A61K 8/34* | (2006.01) |
| *A61K 8/365* | (2006.01) |
| *A61K 8/86* | (2006.01) |
| *A61K 8/02* | (2006.01) |
| *A61K 8/92* | (2006.01) |

(52) U.S. Cl.
CPC ............ *A61K 8/19* (2013.01); *A61K 8/022* (2013.01); *A61K 8/345* (2013.01); *A61K 8/365* (2013.01); *A61K 8/86* (2013.01); *A61K 8/92* (2013.01); *A61Q 19/10* (2013.01); *A61K 2800/43* (2013.01); *A61K 2800/592* (2013.01)

(58) Field of Classification Search
CPC .......... A61K 8/19; A61K 8/345; A61K 8/365; A61K 8/86; A61K 8/042; A61K 8/022; A61K 8/92; A61K 2800/88; A61K 8/0216; A61K 33/10; A61K 2800/432; A61K 2800/42; A61K 2800/592; A61K 2800/43
USPC .......................................................... 510/135
See application file for complete search history.

(56) References Cited

U.S. PATENT DOCUMENTS

| | | | | |
|---|---|---|---|---|
| 6,310,014 | B1 * | 10/2001 | Rau ........................... | A61Q 3/00 134/42 |
| 2006/0099154 | A1 * | 5/2006 | Kahwaty ................ | A61Q 11/00 424/53 |

* cited by examiner

*Primary Examiner* — Eisa B Elhilo
(74) *Attorney, Agent, or Firm* — Lainie E. Parker

(57) ABSTRACT

The color composition formula and method of the present invention uses a color composition to create colorful environments of single or multi-colored hues. It is possible to make the color composition into various different shapes and forms, and they have several different uses as well.

20 Claims, 9 Drawing Sheets

The Color Wheel

The Color Wheel

Primary Colors

Secondary Colors

Tertilary Colors

COLOR COMPOSITION FORMULA AND METHOD

CROSS-REFERENCE TO RELATED APPLICATIONS

This application claims priority based on U.S. Provisional Application No. 62/841,411 filed May 1, 2019, U.S. Provisional Application No. 62/841,433 filed May 1, 2019 and U.S. Provisional Application No. 62/841,443 filed May 1, 2019, and each of which are incorporated by reference herein in their entireties.

FIELD OF THE INVENTION

The present invention is a color composition formula and method. The method uses the color composition formula to create colorful liquid, gel and other semi-solid and solid environments of single or multi-colored hues.

BACKGROUND OF THE INVENTION

Since some of the earliest caveman drawings it is evident that humans have been interested in color. The dyes and pigments they used to stain the walls of the caves can still be seen today.

Color is for most everyone, from young children learning to name the colors and how to make secondary colors from primary colors, as shown on the color wheels in FIGS. 1-4, to fashionistas matching up complimentary colors with color wheels and there's even color therapy to help a person's mood.

The present invention seeks to provide us all, from the young children learning to name colors and having fun in their baths, to older children experimenting with color and solubility, to adults who enjoy a bath, even with other frills like bath salts and moisturizers, to any of us who can benefit from color therapy. To do this, the present invention provides a method for enjoying colors, a unique composition for holding and transporting the colors and a kit to play with colors.

SUMMARY OF THE INVENTION

The color composition formula and method of the present invention uses the color composition to create colorful environments of single or multi-colored hues. It is possible to make the color composition formula into various different shapes and forms, such as powder, tablets, effervescent bath beads, bath tablets, bath bombs, bath fizzier, bath salts and bath powders. Further, some of these formats can be made into various well-known shapes, like berries, bunnies, sharks, flowers, etc.

Regardless of the shape or form, a user can add the color composition to a liquid, gel, other semi-solid material and even some solid-type materials to create colorful liquid, gel and other semi-solid and solid environments of single or multi-colored hues.

One embodiment of the invention is a method of creating a colorful environment comprising the following steps:
a. adding at least one first color composition to at least one of a liquid, gel, semi-solid, or solid, the at least one first color composition comprising a carbonate and/or a bicarbonate of sodium, an add, lactose, and at least one first colored dye;
b. dissolving, in whole or in part, the at least one first color composition in the at least one of a liquid, gel, semi-solid, or solid to create a colorful environment in the at least one of a liquid, gel, semi-solid or solid;
c. determining, during or after the dissolving step of the at least one first color composition, whether the environment has a desired intensity and/or hue of color;
d. adding at least one additional color composition to the at least one of a liquid, gel, semi-solid, solid, if it is determined that the environment does not have the desired intensity and/or hue of color, the at least one additional color composition having the at least one first colored dye and/or at least one other colored dye;
e. dissolving, in whole or in part, the at least one additional color composition in the at least one of a liquid, gel, semi-solid or solid to create a colorful environment in the at least one of a liquid, gel, semi-solid or solid, if the at least one additional color composition is added;
f. determining, during or after the dissolving step of the at least one additional color composition, whether the environment has a desired intensity and/or hue of color, if the at least one additional color composition is dissolved; and
g. repeating steps d. through f. if it is determined that the environment does not have the desired intensity and/or hue of color.

Another embodiment of the invention is a color composition comprising:
a composition comprising the following formula:
sodium carbonate in a range of from about 30 to about 45%,
sodium bicarbonate in a range of from about 20 to about 35%,
citric acid in a range of from about 15 to about 35%,
lactose in a range of from about 5 to about 25%, and
dye in a range of from about 0.5 to about 3%; and
about 0.1 to about 5% of at least one of the following:
cocoa butter, avocado oil, sunflower oil, polyethylene glycol, flowers, flower buds, tea leaves, lavender, lavender buds, roses, shea butter, glitter, flower petals, skin conditioning oils, cleansers, skin-conditioning plant oils, essential oils, mineral oils, aroma therapy oils, oatmeal, milk, honey, fragrance, perfumes, Epsom salt, sea salt and/or soap.

Still another embodiment of the invention is a color kit comprising:
at least one color composition comprising the following formula:
sodium carbonate in a range of from about 30 to about 45%,
sodium bicarbonate in a range of from about 20 to about 35%,
citric acid in a range of from about 15 to about 35%,
lactose in a range of from about 5 to about 20%, and
at least one dye in a range of from about 0.5 to about 3%; and
about 0.1 to about 5% of at least one of the following:
cocoa butter, avocado oil, sunflower oil, polyethylene glycol, flowers, flower buds, tea leaves, lavender, lavender buds, roses, shea butter, glitter, flower petals, skin conditioning oils, cleansers, skin-conditioning plant oils, essential oils, mineral oils, aroma therapy oils, oatmeal, milk, honey, fragrance, perfumes, and/or soap;
and
bath salts, a color wheel (see, for example, the color wheel in FIGS. 1-4), a conventional (as conventional(ly) is defined in the DEFINITIONS section in the DETAILED DESCRIPTION OF THE INVENTION section) paint brush, at least one conventional container for holding at least one color composition together with a liquid, gel, semi-solid and/or solid environment, a conventional ice cube tray, a container of at least one color composition in powder form (any known or conventional container for powder, e.g., a shaker, a paper or plastic packet, a jar, etc.), a container for dipping an egg into a combination of at least one color composition and a liquid, gel, semi-solid and/or solid environment (a conventional egg-dipping container, such as those used for Easter eggs), a conventional egg container or crate for storing and transporting eggs, a dropper (like a medicine dropper) or similar device for transferring and mixing colors in liquid, gel, or other semi-solid form so that the user can attain the desired intensity and/or hue of color when using more than one color or different amounts (intensities) of the same color (any conventional dropper or device can be used), and/or one or more pieces of plain paper and/or pre-printed paper, as conventionally used by inexperienced and experienced artists alike.

BRIEF DESCRIPTION OF THE DRAWINGS

FIG. 12 B is a hatch pattern representing blue in the figures;

FIG. 12 C is a hatch pattern representing green in the figures;

FIG. 12 D is a hatch pattern representing yellow or gold in the figures;

FIG. 12 E is a hatch pattern representing orange in the figures;

FIG. 12 F is a hatch pattern representing red or pink in the figures;

FIG. 12 G is a hatch pattern representing brown in the figures;

FIG. 12 H is a hatch pattern representing black in the figures; and

FIG. 12 I is a hatch pattern representing grey or silver in the figures.

DETAILED DESCRIPTION OF THE INVENTION

The invention is centered on the user creating a colorful environment of a desired intensity and/or hue of color. The method of the invention accomplishes this using one or more of the color compositions having one color of dye or different colored dyes. Generally, speaking, the intensity of a single color is increased when more color composition of a single color is used, while the hue is changed when different colors are mixed together. That being said, the intensity of color increases when more color composition is used, no matter which color.

Figure 1:
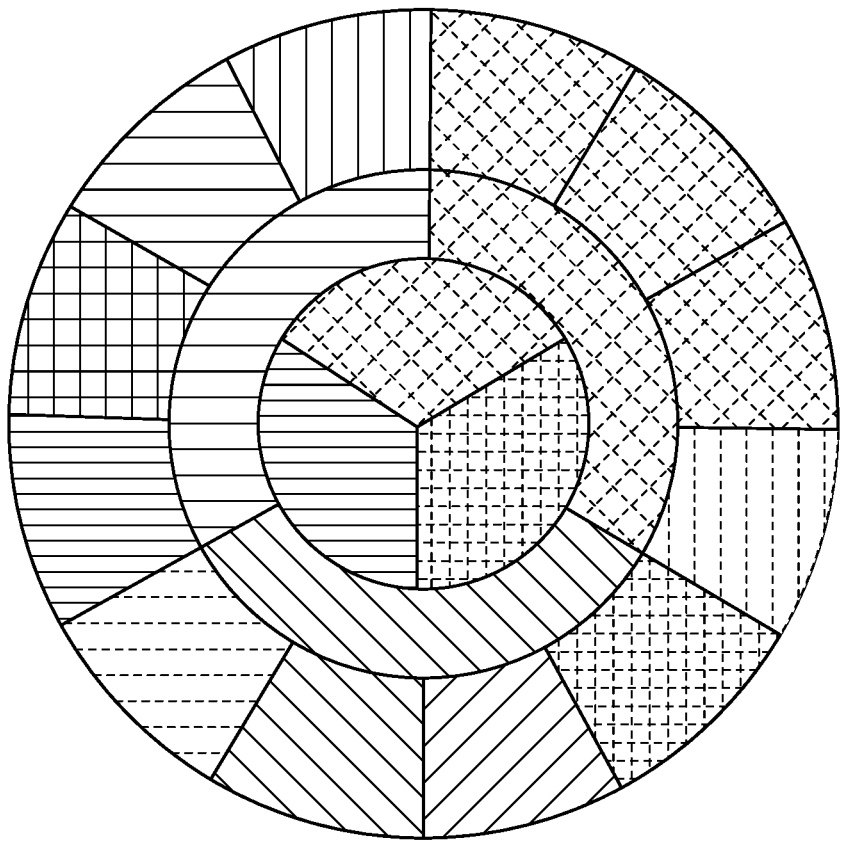
FIG. 1 is a color wheel displaying the primary, secondary and tertiary colors.
Figure 2:
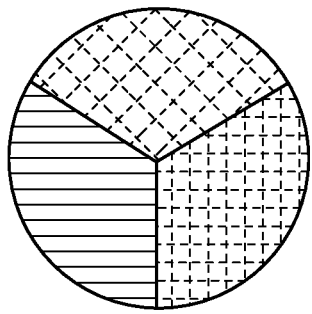
FIG. 2 displays the primary colors portion of the color wheel of FIG. 1.
Figure 3:
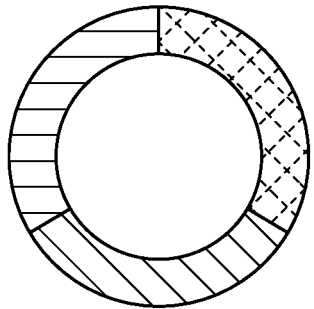
FIG. 3 displays the secondary colors portion of the color wheel of FIG. 1.

The invention is thus a delightful, colorful experience for the user as well as an educational one to learn about primary, secondary and tertiary colors. The color wheel shown in FIG. 1 shows all of these different types of colors and the color composition used in the invention can be made in each of these colors. When a user has only primary colors, see FIG. 2, of the inventive color composition, then those primary colors can be used to make the secondary colors shown in FIG. 3.

For example:

TABLE 1

| PRIMARY COLORS | RESULTING SECONDARY COLOR |
| --- | --- |
| RED + BLUE = | PURPLE |
| RED + YELLOW = | ORANGE |
| BLUE + YELLOW = | GREEN |

Figure 4:
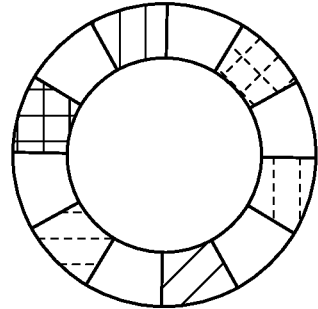
FIG. 4 displays the tertiary colors portion of the color wheel of FIG. 1.
Figure 5:
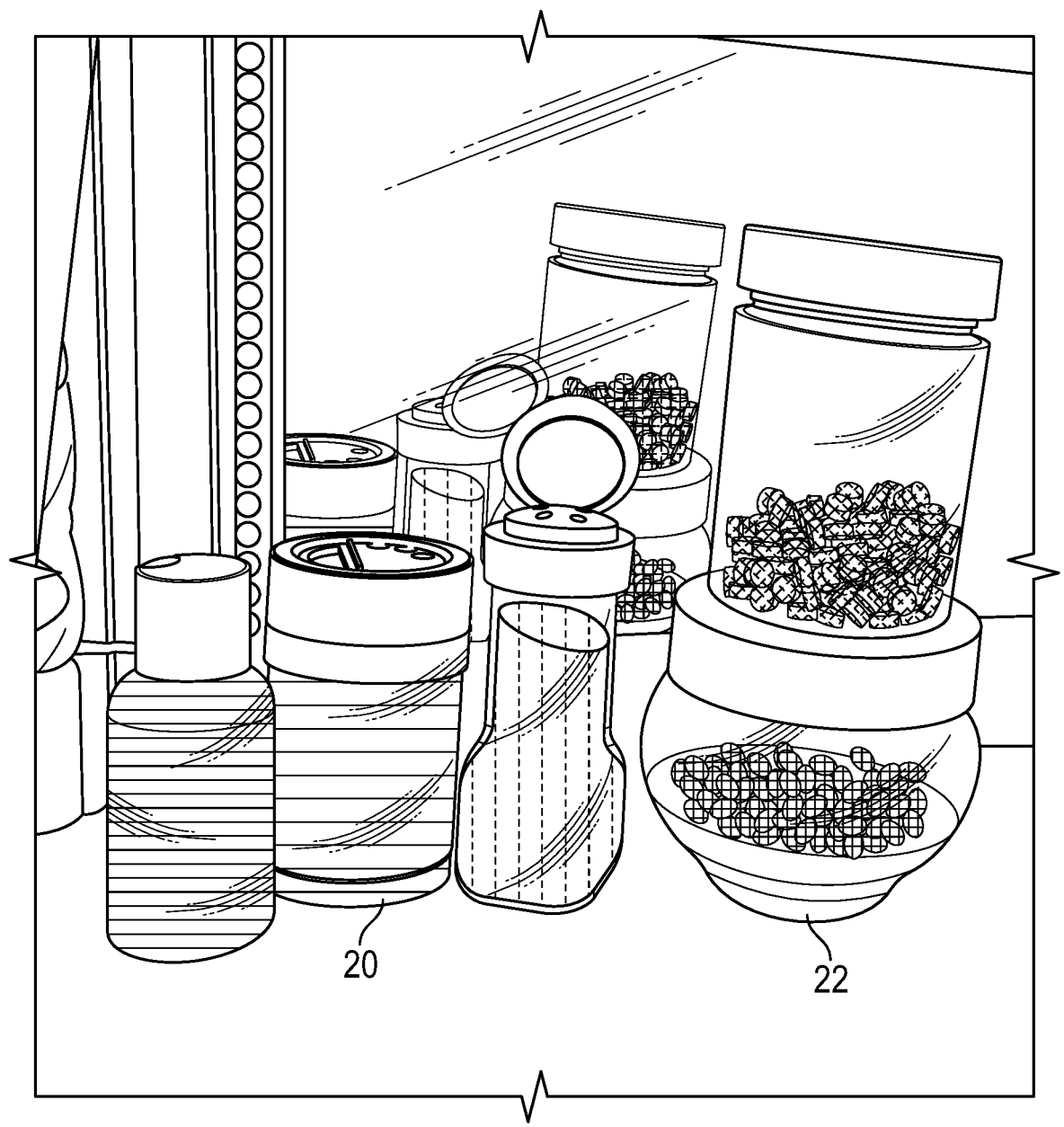
FIG. 5 displays containers with the powder and tablet form of the color composition formula of the invention and which is used in the methods of the invention.

Then, if desired, the user can take the primary and secondary colors to make the tertiary colors shown in FIG. 4.

For example, see Table 2:

TABLE 2

| PRIMARY + SECONDARY | RESULTING TERTIARY COLOR |
| --- | --- |
| RED + ORANGE = | RED-ORANGE |
| YELLOW + ORANGE = | YELLOW-ORANGE |
| YELLOW + GREEN = | YELLOW-GREEN |
| BLUE + GREEN = | BLUE-GREEN |
| BLUE + PURPLE = | BLUE-PURPLE |
| BLUE + RED = | BLUE-RED |

The secondary and tertiary colors can be made by mixing equal parts of each color from the first column of the tables shown above. However, using more of one color than another will provide a different hue, the shade of which (and how much more one color to use) is to be determined by the user's desire. The outer wheel of the color wheel in FIG. 1 shows the primary, secondary and tertiary colors.

In a first embodiment, the invention is a method of creating a colorful environment comprising the following steps:

a. adding at least one first color composition to at least one of a liquid, gel (as defined in the DEFINITIONS section of this part of the specification), semi-solid, or solid (these are some of the choices of the environment as defined in the DEFINITIONS section of this DETAILED DESCRIPTION OF THE INVENTION section), it is further noted that the liquid, gel, semi-solid, or solid can include water as an ingredient or even be water, e.g., the liquid can be water or something containing water, e.g., isopropyl alcohol (93%, 99%, etc.), and the solid can be ice, the gel can be hair gel, jello, etc.

also, if the user is simply experimenting, then the color composition is likely being added to at least two of the liquid, gel, semi-solid, or solid, for which containers can be included in a kit with the color composition, however, if the user is taking a bath, and likely experimenting in the bath, then the color composition is likely being added to liquid water, the at least one first color composition comprising a carbonate and/or a bicarbonate of sodium, an add (e.g., potassium bitartrate, apple cider vinegar, citric add, white vinegar, lemon juice, etc.), lactose, and at least one first colored dye;

b. dissolving, in whole or in part, the at least one first color composition in the at least one of a liquid, gel, semi-solid, or solid to create a colorful environment in the at least one of a liquid, gel, semi-solid or solid;

c. determining, during or after the dissolving of the at least one first color composition, whether the environment has a desired intensity and/or hue of color;

d. adding at least one additional color composition to the at least one of a liquid, gel, semi-solid, or solid, if it is determined that the environment does not have the desired intensity and/or hue of color, the at least one additional color composition having the at least one first colored dye and/or at least one other colored dye;

e. dissolving, in whole or in part, the at least one additional color composition in the at least one of a liquid, gel, semi-solid or solid to create a colorful environment in the at least one of a liquid, gel, semi-solid or solid, if the at least one additional color composition is added;

f. determining, during or after the dissolving step of the at least one additional color composition, whether the environment has a desired intensity and/or hue of color, if step d. and/or step e. occurs; and g. repeating steps d. through f. if it is determined that the environment does not have the desired intensity and/or hue of color.

This first embodiment can further comprise the following steps:

h. adding at least one second color composition to the at least one of a liquid, gel, semi-solid, or solid, the second color composition comprising at least one second colored dye (it can also comprise a carbonate and/or a bicarbonate of sodium, an acid, and lactose);

i. dissolving, in whole or in part, the at least one second color composition in the at least one of a liquid, gel, semi-solid, or solid to create a colorful environment in the at least one of a liquid, gel, semi-solid or solid;

j. determining, during or after the dissolving of the at least one second color composition, whether the environment has a desired intensity and/or hue of color;

k. adding at least one other additional color composition to the at least one of a liquid, gel, semi-solid, solid, if it is determined that the environment does not have the desired intensity and/or hue of color, the at least one other additional color composition having the at least one second colored dye and/or at least one other colored dye;

l. dissolving, in whole or in part, the at least one other additional color composition in the at least one of a liquid, gel, semi-solid or solid to create a colorful environment in the at least one of a liquid, gel, semi-solid or solid, if the at least one other additional color composition is added;

m. determining, during or after the dissolving step of the at least one other additional color composition, whether the environment has a desired intensity and/or hue of color, if the at least one other additional color composition is dissolved and/or, if steps k. and or l. occur; and n. repeating steps k. through m. if it is determined that the environment does not have the desired intensity and/or hue of color.

In this first embodiment, prior to adding either or all of the at least one first color composition, the at least one additional color composition and/or the at least one second color composition to the at least one of a liquid, gel, semi-solid, or solid, it is possible to have an additional step comprising forming these color compositions into a powder, tablet, bath bomb or bath bead (as defined in the DEFINITIONS section of this part of the specification).

As noted above, in addition to tablet and powder form, the color composition formulation can be made into any type of shape desired. For example, in the same fashion it is molded into tablet form (which can be the same way medicine is molded into tablets), it can be molded into a spherically shaped bath bomb of any size, usually ranging in diameter from 1 to 3 or even 5 inches. It can also be molded into any shape, such as a duck (which might be yellow), or a strawberry (which might be red). It would be visually appealing to have, for example, a purple grape cluster-shaped color composition formulation, or one in the shape of a blue sailboat.

The amount of color composition and color dye used in the method depends entirely on the user and the type of activity. The amount can be increased or decreased depending on whether the user determines that the environment has the desired intensity of color, or not. And the dye can be chosen depending on whether the user determines that the environment has the desired intensity and/or hue or not.

In one example, the tablets are made in a small size and a large size. In this example:

1 small tablet=0.365 grams
1 large tablet=2.8 grams
Average use would be 1 small tablet per 0.365 per liter of water.

So, if in this embodiment of the invention, the method included painting watercolors on a small piece of paper, then probably 1 small tablet in a small cup of water would be sufficient. However, if the user desires to color a bath, then probably more tablets would be desired. For example:

Hues and Shade Intensity

| | | |
|---|---|---|
| Light shades | 4 tabs @.365 g = 1.46 g | (2-3 year old, who will have less water in the tub) |
| Medium shades | 20 tabs @.365 g = 7.3 g | older child 6-10 |
| Intense shades | 30 tabs @.365 g = 9.12 g | older child or adult |

Of course, more or fewer tablets can be used depending on the user's preference.

When using larger tablets (2.92 g), you use fewer tablets:
2 to 8 tablets per bath
1 to 2 tablets per child
12 to 15 shakes of powder, which is about 12 to 15 tablets for adults
Of course, more or fewer tablets can be used depending on the user's preference.

In a kit, bath salts can be mixed with one sized or varying sized tablets and packaged in the same container or jar. For example, a package can include about 100 of the smaller tablets (0.365 g) for about 2 Lbs of salt. Alternatively, a package can include 50 to 200 tablets of varying sizes, small and large tablets (2.92 g), for about 2 Lbs of salt. For a bath, a user can use as much salt and tablets as desired, e.g., 1-2 cups of salt with tablets, per bath.

In any event however, when the larger tablets are used, then fewer tablets are likely to be desired, since there are approximately 7 to 8 of the smaller tablets @0.365 g=2.55 g/2.92 g for each large tablet.

When any of the color compositions are formed into a powder, this embodiment also adds the additional step of shaking the powder out of its container prior to the step of adding it to the at least one of a liquid, gel, semi-solid, or solid. Also, when the color composition is a powder, the intensity of the color is greatly magnified. Accordingly, when the color composition is going to be formed into a powder, the amount of dye can be greatly reduced and/or the amount of color composition in the shaker can be reduced and some other known and conventional bulk-adding bath product additives can be used, e.g., clays, starch, etc.

As with the tablets, the amount of the powder used depends entirely on the user and the type of activity. The amount can be increased or decreased depending on whether the user determines that the environment has the desired intensity of color, or not. And the dye can be chosen depending on whether the user determines that the environment has the desired hue or not.

As a general rule:
1 shake is about 1 tablet, or about 0.365 g (one tablet per shake)
4 shake is about 4 tablets, or about 1.46 g for a child of age 2 to 3

The powder is wonderful to use because it dissolves and fizzes really quickly. Also, what's really nice about the powder is that it can all have the same color composition with the same dye in a single container or one single container of powder can have more than color composition with more than one dye. When a color composition having the same dye is in one container, shaking out the powder produces a single color on contact with the chosen environment (liquid, gel, semi-solid, or solid) and with at least partial dissolution or reaction of one or more components of the color composition, and shaking out more powder increases the intensity of that color. However, when color compositions having different colored dyes are in one container, shaking out powder can increase the intensity of one color and also change the hue of the colors (change the colors) being shaken out. Also, when color compositions having different colored dyes are in one container, every time you shake you get a new, colorful result, so that there is an infinite possibility of everchanging colorful kaleidoscopes at your fingertips.

Further, in this first embodiment, the composition of the at least one first color composition, the at least one additional color composition, the at least one second color composition and/or the at least one other additional color composition can comprise:
sodium carbonate, e.g., soda ash, e.g., dense soda ash, in a range of from about 30 to about 45%, about 33 to about 38%, about 35 to about 40%, about 36 to about 41%,
sodium bicarbonate in a range of from about 20 to about 35%, about 23 to about 25%, about 24 to about 30%,
citric acid in a range of from about 15 to about 35%, about 20 to about 30%, about 18 to about 25%, about 19 to about 22%,
lactose in a range of from about 5 to about 20%, about 10 to about 12%, about 11 to about 12%, about 10 to about 15%, and
dye in a range of from about 0.5 to about 3%, about 0.5 to about 2%, about 1 to about 1.5%.

The composition can also include about 0.1 to about 5%, or as much or as little as desired, of at least one of the following:
cocoa butter, avocado oil, sunflower oil, polyethylene glycol, flowers, flower buds, tea leaves, lavender, lavender buds, roses, shea butter, glitter, flower petals, skin conditioning oils, cleansers, skin-conditioning plant oils, essential oils, mineral oils, aroma therapy oils, oatmeal, milk, honey, fragrance, perfumes, Epsom salt, sea salt and/or soap.

Another embodiment of the invention is a color composition comprising:
a composition comprising:
sodium carbonate, e.g., soda ash, e.g., dense soda ash, in a range of from about 30 to about 45%, about 33 to about 38%, about 35 to about 40%, about 36 to about 41%,
sodium bicarbonate in a range of from about 20 to about 35%, about 23 to about 25%, about 24 to about 30%,
citric acid in a range of from about 15 to about 35%, about 20 to about 30%, about 18 to about 25%, about 19 to about 22%,
lactose in a range of from about 5 to about 20%, about 10 to about 12%, about 11 to about 12%, about 10 to about 15%, and
dye in a range of from about 0.5 to about 3%, about 0.5 to about 2%, about 1 to about 1.5%; and
about 0.1 to about 5%, or as much or as little as desired, of at least one of the following: cocoa butter, avocado oil, sunflower oil, polyethylene glycol, flowers, flower buds, tea leaves, lavender, lavender buds, roses, shea butter, glitter, flower petals, skin conditioning oils, cleansers, skin-conditioning plant oils, essential oils, mine al oils, aroma therapy oils, oatmeal, milk, honey, fragrance, perfumes, Epsom salt, sea salt and/or soap.

Additionally, some alternatives to sodium bicarbonate include, but are not limited to sodium sesquicarbonate, and carbonates of sodium, calcium, or magnesium. However, it is not known how well these work as compared with the examples disclosed herein.

Further alternatives to citric add include substituting 1 tablespoon of lemon juice or white distilled vinegar for every ½ teaspoon of citric acid. Other alternatives include, but are not limited to apple cider vinegar, cream of tartar (potassium bitartrate), and white vinegar, but it is not known whether any of these alternatives to citric acid work as well as the examples disclosed herein.

The color composition of this embodiment can be in the form of a powder, tablet, bath bomb or bath bead. In any event, it is good to keep them dry since they are meant to react with moisture. For this reason, it is usually advisable to avoid adding humectants like glycerin and sodium lactate to such a composition because they will attract water to the product.

Further, the color composition of this embodiment can also include at least one other composition comprising the following formula:
sodium carbonate in a range of from about 36 to about 41%, sodium bicarbonate in a range of from about 23 to about 25%,
citric acid in a range of from about 18 to about 25%,
lactose in a range of from about 10 to about 12%, and
another dye in a range of from about 0.5 to about 2%; and
wherein the at least one other composition is in the form of a powder, tablet, bath bomb or bath bead.

Still another embodiment of the invention is a color kit comprising:
at least one color composition comprising:
sodium carbonate, e.g., soda ash, e.g., dense soda ash, in a range of from about 30 to about 45%, about 33 to about 38%, about 35 to about 40%, about 36 to about 41%,
sodium bicarbonate in a range of from about 20 to about 35%, about 23 to about 25%, about 24 to about 30%,
citric acid in a range of from about 15 to about 35%, about 20 to about 30%, about 18 to about 25%, about 19 to about 22%,
lactose in a range of from about 5 to about 20%, about 10 to about 12%, about 11 to about 12%, about 10 to about 15%, and
dye in a range of from about 0.5 to about 3%, about 0.5 to about 2%, about 1 to about 1.5%; and
about 0.1 to about 5%, or as much or as little as desired, of at least one of the following: cocoa butter, avocado oil, sunflower oil, polyethylene glycol, flowers, flower buds, tea leaves, lavender, lavender buds, roses, shea butter, glitter, flower petals, skin conditioning oils, cleansers, skin-conditioning plant oils, essential oils, mineral oils, aroma therapy oils, oatmeal, milk, honey, fragrance, perfumes, and/or soap;
and
bath salts.

Some examples of the milk include cow's, goat's, almond, cashew or coconut milk. Combinations of any of these types of milk or dried versions of these types of milk can also be used.

Some examples of bath salts include Epsom salt and sea salt, and, more specifically, dead sea salt. As discussed above, there is no set amount of tablets and sea salt or Epsom salt, and the kit is no different. One example is to include 100 tablets in a 2 lb. bag of salt.

For example:
0.365 g tablets×100 tablets=36.5 g=1.29 oz tabs for the salts in a 2 lb. bag.

Additionally, when the kit includes color composition in powder form, it is recommended to package the powder separately from the salt. However, there is no limit on the amount of salt or powder included in the kit or to be used by the user. The only size limit for the kit would be the undesirability of having a kit be too large or too small.

The color kit can include at least one other color composition comprising the following formula:
sodium carbonate in a range of from about 36 to about 41%,
sodium bicarbonate in a range of from about 23 to about 25%,
citric acid in a range of from about 18 to about 25%,
lactose in a range of from about 10 to about 12%, and
another dye in a range of from about 0.5 to about 2%.

In the color kit, the at least one color composition and the at least one other color composition can be in the form of a powder, tablet, bath bomb or bath bead.

When either the at least one color composition or the at least one other color composition are in the form of a powder, they are usually in their own container, or in a separate chamber within the kit, because powder is so difficult to contain. It gets over everything.

The color kit can include several different items, such as a color wheel or at least one paint brush.

Figure 6:
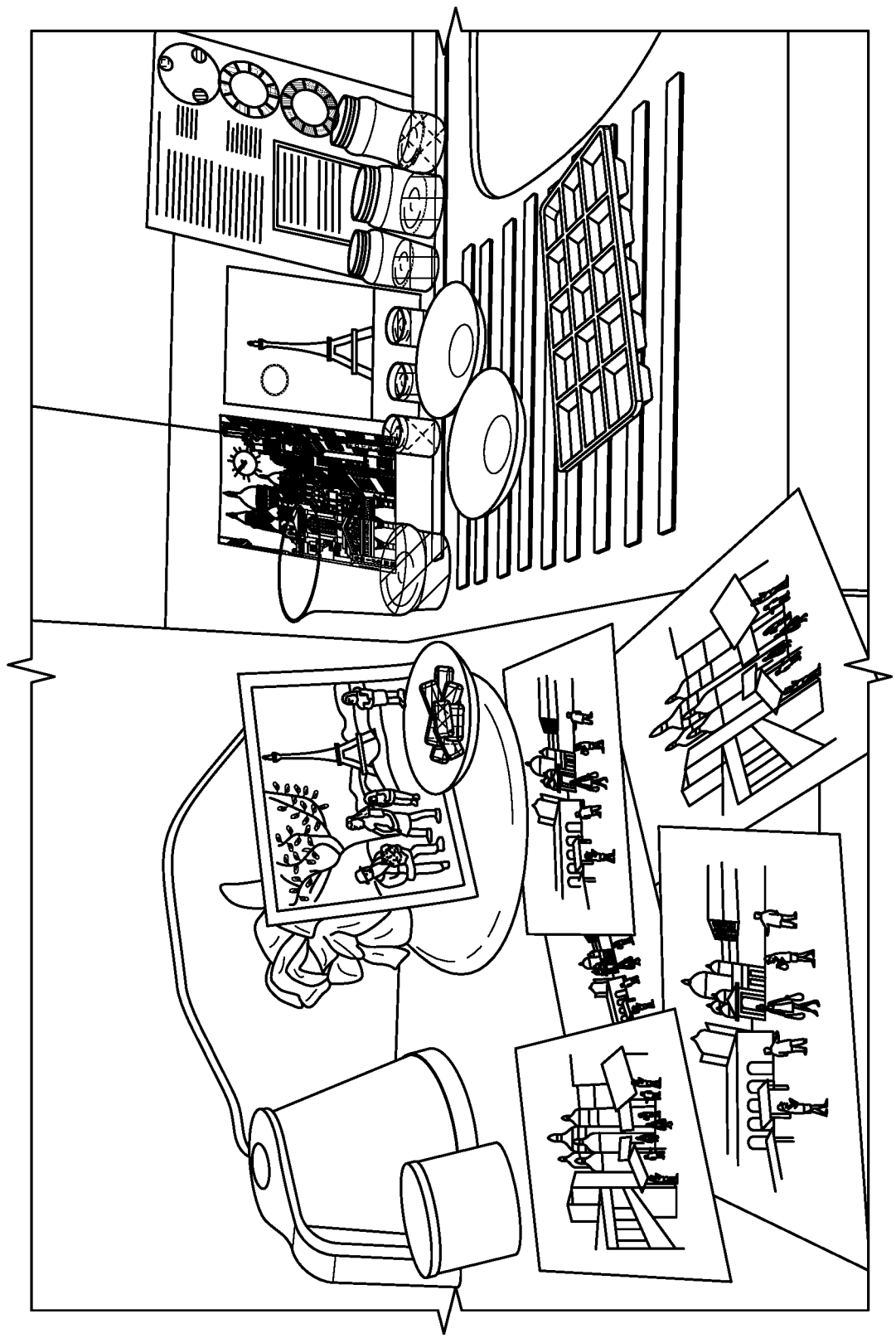
FIG. 6 shows watercolor art made using the invention with pre-printed paper, and also displays ice cubes of the dispersed color composition and jars of the color composition dispersed in liquid.
Figure 7:
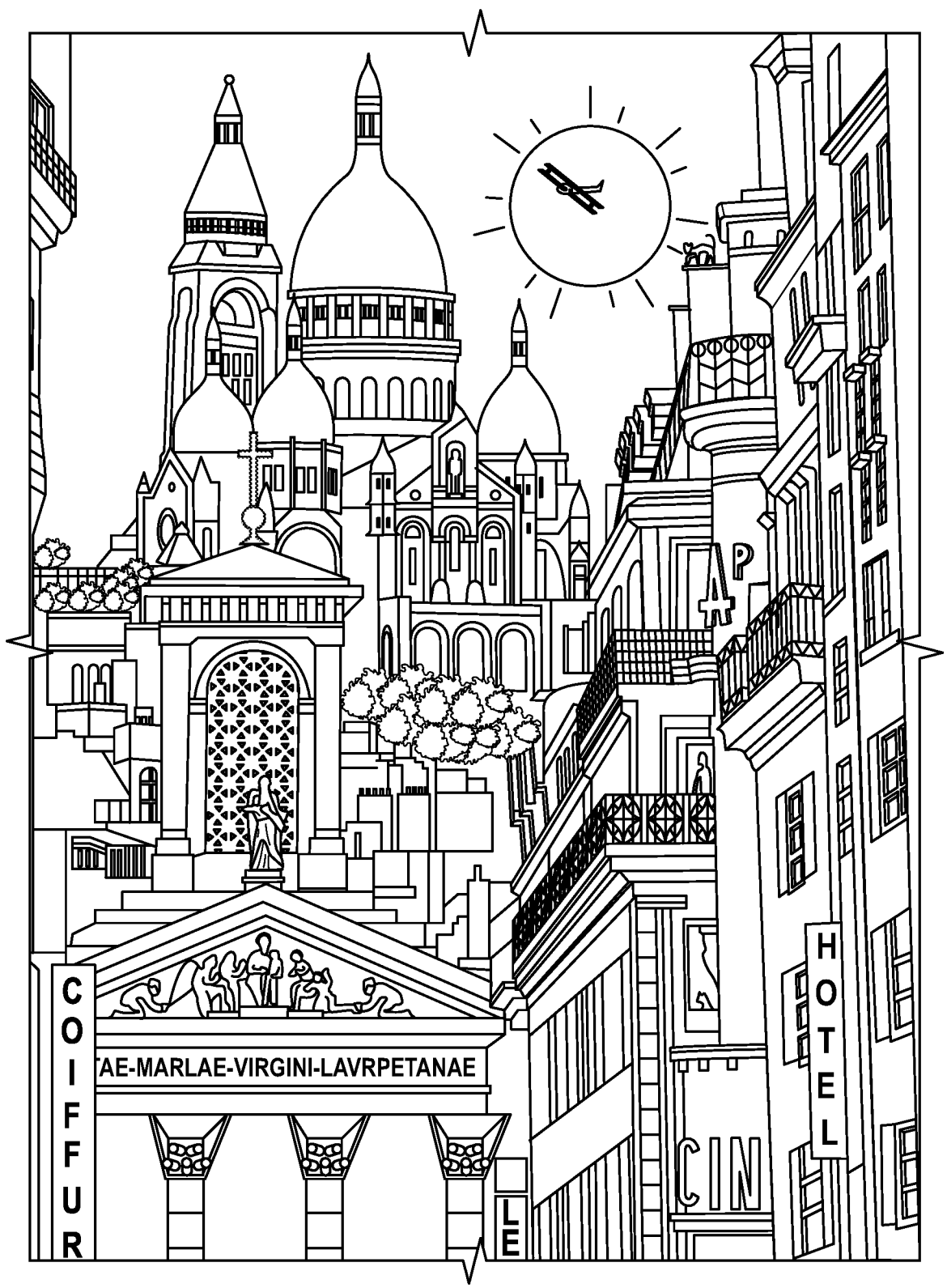
FIG. 7 is an example of a paper card pre-printed with a scene.
Figure 8:
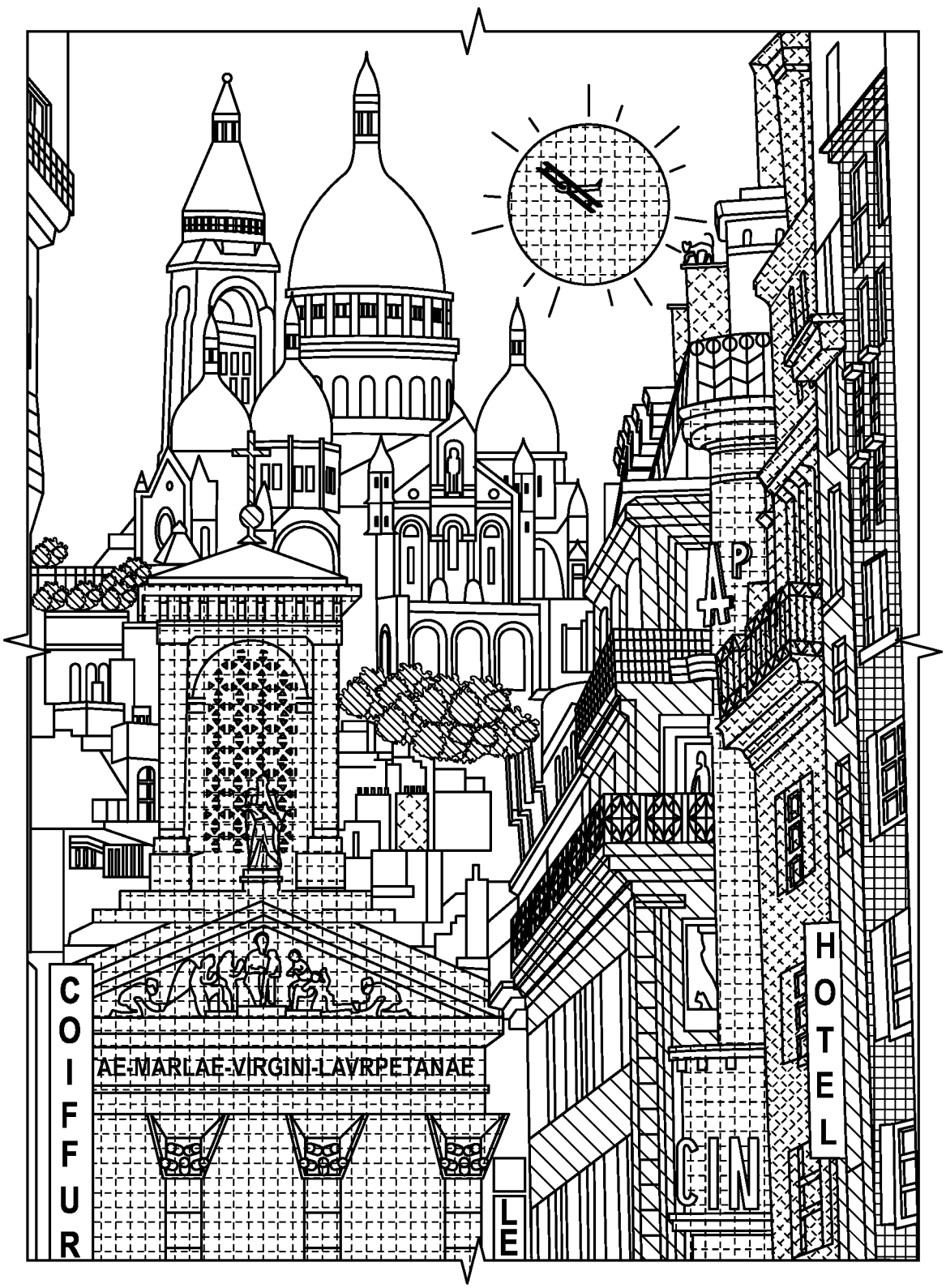
FIG. 8 is a finished watercolor of the pre-printed card of FIG. 7 created using the invention.
Figure 9:
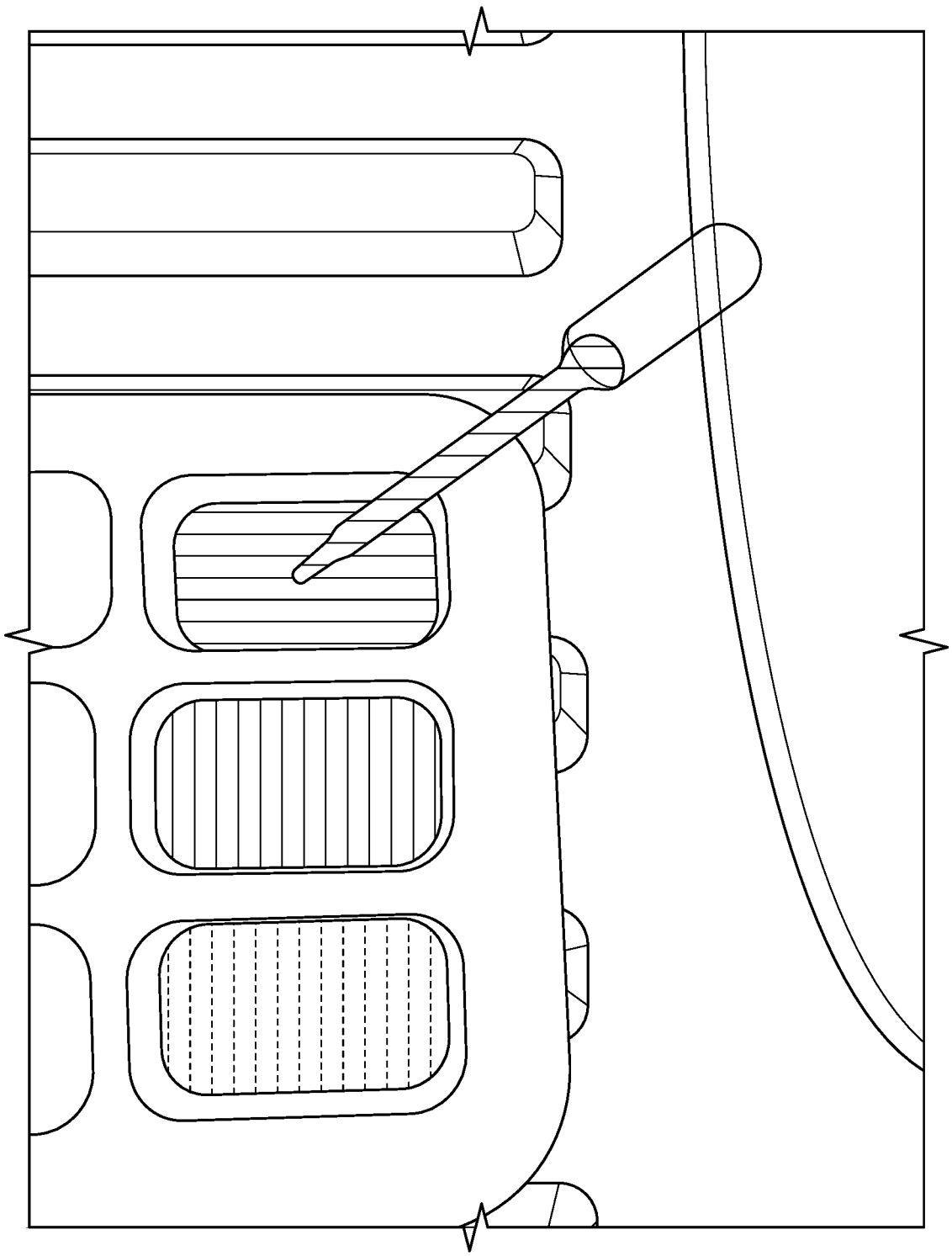
FIG. 9 shows a dropper being used to transfer some blue liquid made with the composition of the invention, and shows the blue liquid along with some red and yellow liquid in a multi-compartment holding container.
Figure 10:
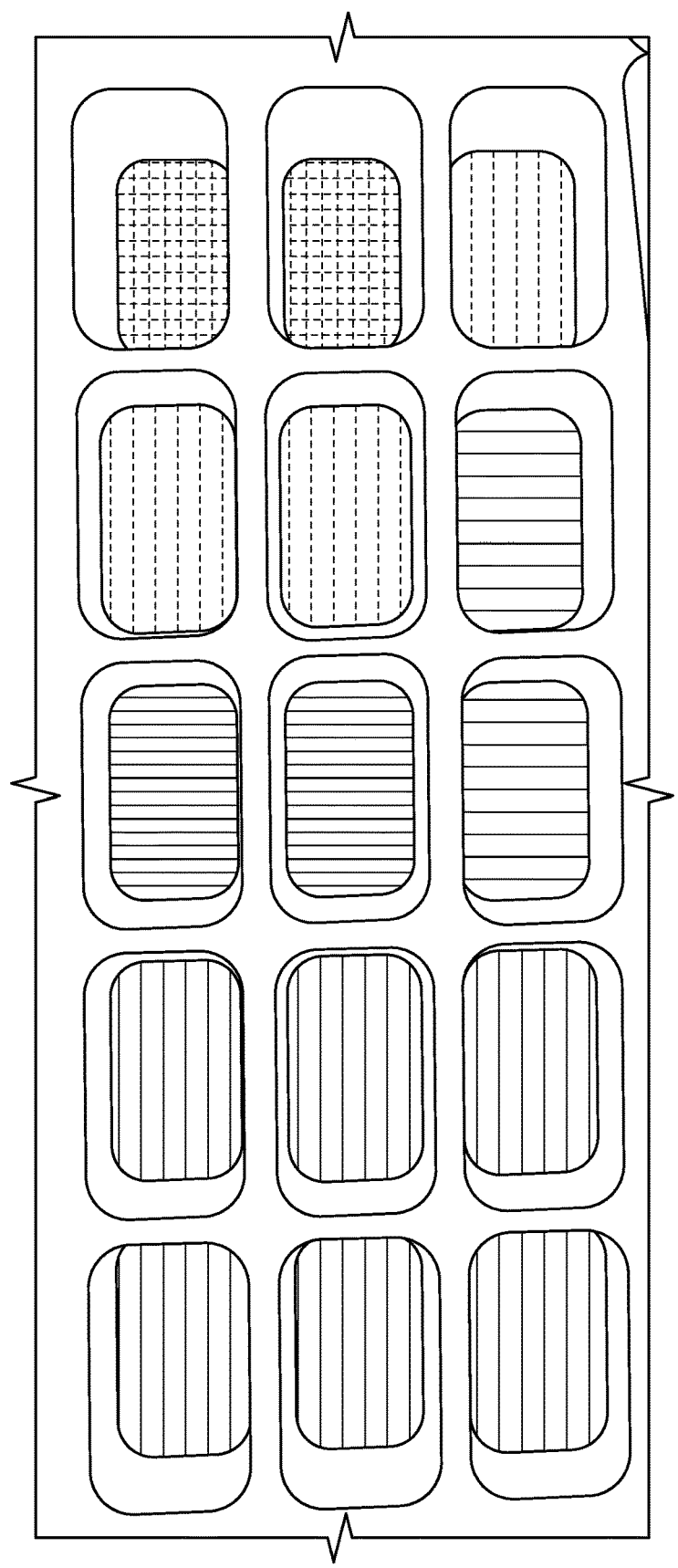
FIG. 10 shows another example of a multi-compartment holding container, specifically an ice cube tray, and it is filled with colorful liquid made with the composition of the invention, specifically, yellows and orange-yellows, lighter blues and darker blues, reds, shades of pink and purple-reds.
Figure 11:
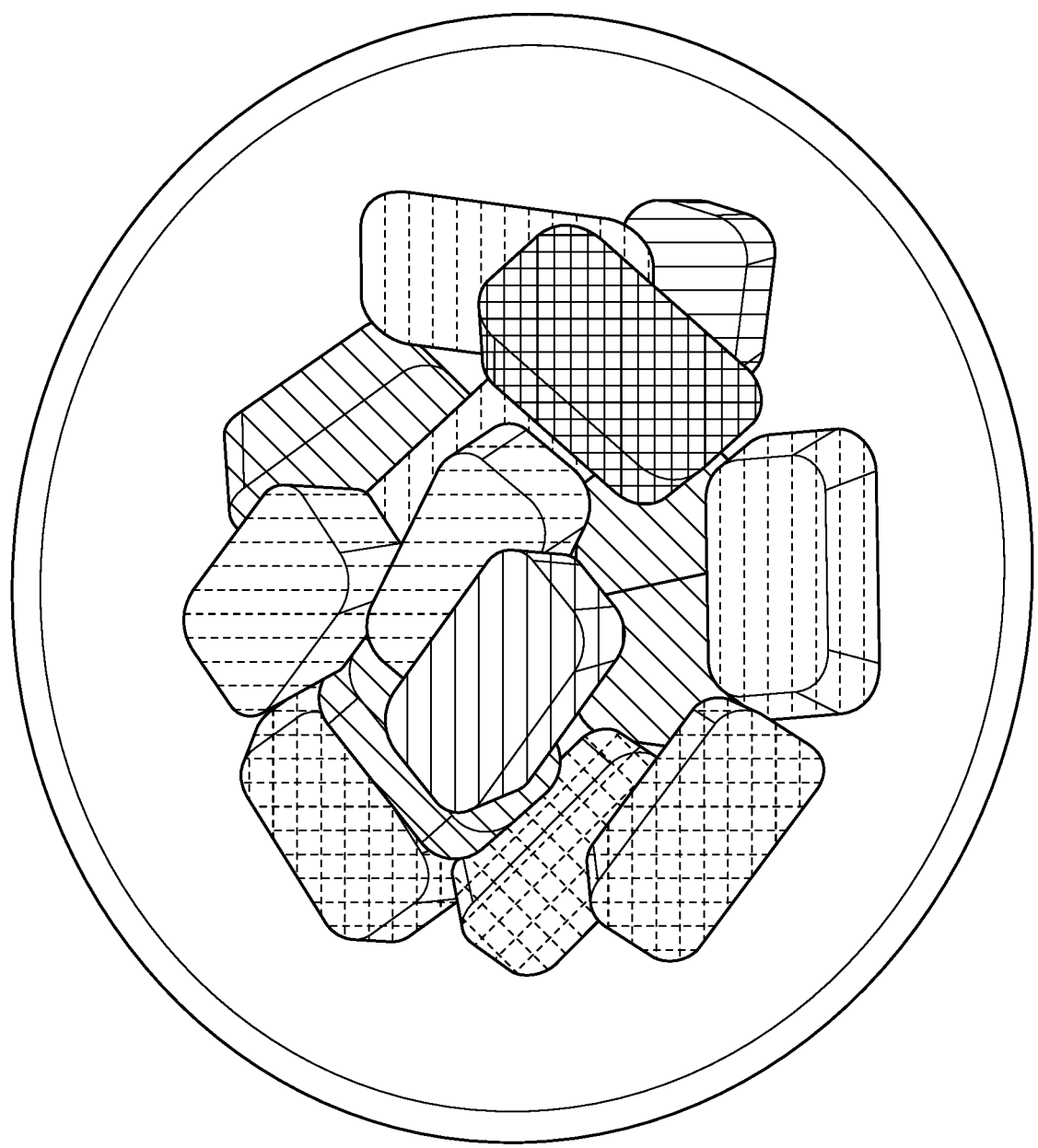
FIG. 11 shows a beautiful bowl of ice cubes made using the invention, it includes the steps of the method of adding the color composition to and dissolving the color composition on or in a liquid, gel and/or other semi-solid environment and freezing it, or it includes the steps of the method of adding the color composition to and dissolving the color composition on or in an ice cube or other frozen solid, the example shown in this FIG. has ice cubes in the bowl of varying colors and shades of green (lighter green, darker green, grass green, swamp green, yellow-green), of gray, of purple, orange and even turquoise.
Figure 12A:
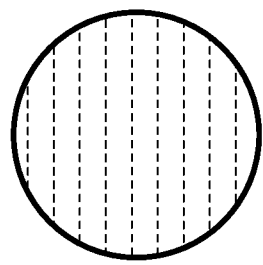
FIG. 12 A is a hatch pattern representing purple or violet in the figures.
Figure 12B:
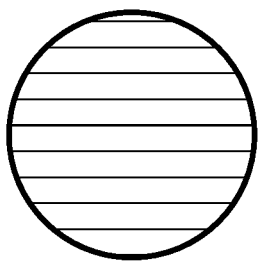
Figure 12C:
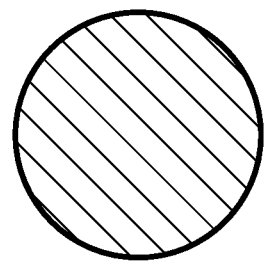
Figure 12D:
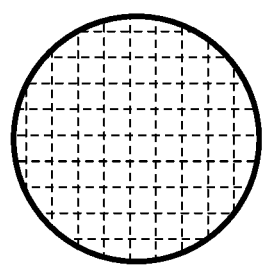
Figure 12E:
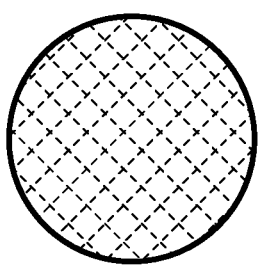
Figure 12F:
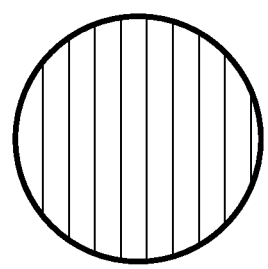
Figure 12G:
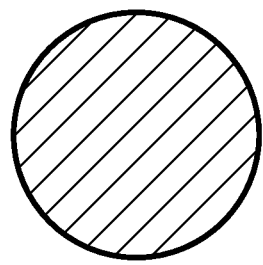
Figure 12H:
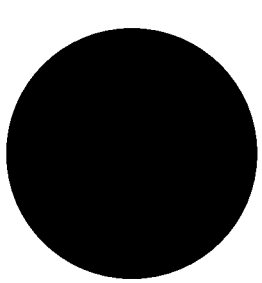
Figure 12I:
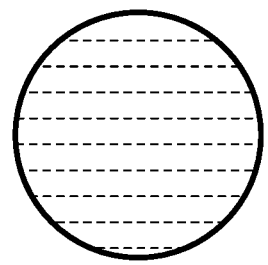

The color kit can include paper and the paper can be pre-printed with a scene. See, e.g., FIGS. 6-8. Then the user can simply use the color composition according to the method to combine it with one of the environments and make "water colors" to fill in the scene as desired, usually with a paint brush discussed above. FIG. 11 shows the color composition in a solid (ice) environment, from which the dye in the color composition can be used as "water colors". The color kit can also include a container for the liquid, gel, semi-solid, and/or solid. An example of a simple container is a petri dish, or something similar, or a small cup, like a Dixie® cup. Other containers can be larger cups or multi-sectional containers, or palettes used for water colors. In one embodiment, the container can be an ice cube tray, which works rather nicely as a multi-sectional container for holding more than one color, as shown in FIG. 10. Also, with an ice cube tray, the water colors can be made before use, frozen and then used while they are thawing out. Additional color compositions can also be added to the ice cubes to increase the color's intensity and/or change the hue. Such fun for a user at any age to apply a paint brush, or other painting-type utensil, to an ice cube for color to paint, and to watch the ice cube as it melts. This is also educational, especially for the younger users.

As discussed herein, the color composition of the claimed invention can be used in effervescent bath beads, bath tablets, bath bombs, bath fizzier, bath salts and bath powders. It is also possible to formulate this composition so that it is non-staining, and can be used without any added fragrance, perfumes or soap, so that it is safer for the user by avoiding these known allergy-causing substances. Additionally, it can be made with or without using an oil additive.

When the effervescent tablets begin to dissolve in water, they create streams of color in the water, the intensity of which can be controlled by the user depending on how many tablets (or how much powder) is used. In addition to controlling the intensity of the color, the user can control the hues and shades of colors as well. For example, when using tablets and/or powder in two or more of the primary colors of red, blue and or/yellow, the combination creates secondary colors of purple, green and/or orange, depending on which colors are combined. Of course, the tablets and/or powder can be a choice of any colors, for example, if purple, green and/or orange are use, then combinations of those colors create tertiary colors. The tablets and/or powder can be every color of the rainbow and the user can mix them in different ratios or quantities of tablets and/or powder and water to create many different hues, shades and intensities.

While the powder can be dispensed in single color containers, as shown in FIG. 4, the powder can also be a mixture of colors in a single container so that different colors are shaken out of the container together and begin to create all different combinations of color in the water. This aspect of the invention is explained in more detail below with reference to the color wheel of FIG. 1 and is a beneficial education aspect as well. One benefit of the inventive method and product is that it is educational.

Example 1 (Formula)

| MIX SIZE | |
|---|---|
| Soda Ash | 40.830% |
| Bicarbonate | 24.000% |
| Lactose | 11.570% |

-continued

| | |
|---|---|
| Citric Acid | 19.695% |
| Mineral Oil | 0.105% |
| Dye | 1.200% |
| Poly ethylene glycol (PEG) | 2.600% |
| TOTAL | 100.000% |

| DYE (one or more) |
|---|
| Blue Dye #1 |
| Yellow Dye #5 |
| Red Dye #33 |

Example 2 (Formula)

| MIX SIZE | |
|---|---|
| Dense Soda Ash | 36.525% |
| Sodium Bicarbonate | 24.000% |
| Citric Acid | 24.000% |
| Lactose | 11.570% |
| Carbowax (PEG3350) | 2.600% |
| Dye | 1.200% |
| Mineral Oil | 0.105% |
| TOTAL | 100.000% |

| DYE (one or more) |
|---|
| Blue Dye #1 |
| Yellow Dye #5 |
| Red Dye #33 |

Example 3 (Formula)

| MIX SIZE | |
|---|---|
| Dense Soda Ash | 36.630% |
| Sodium Bicarbonate | 24.000% |
| Citric Acid | 24.000% |
| Lactose | 11.570% |
| Carbowax (PEG3350) | 2.600% |
| Dye | 1.200% |
| TOTAL | 100.000% |

| DYE (one or more) |
|---|
| Blue Dye #1 |
| Yellow Dye #5 |
| Red Dye #33 |

Although these examples utilize one of the specific dyes listed above, any other available or newly made dyes can be used in the invention. Generally, water soluble and/or food safe dyes are used. Most users prefer to have healthy options. Also, water soluble colors are less likely to leave any color residue behind when finished using the composition.

Definitions

Bath beads—gel-like capsules filled with oil among other substances. They have an outer membrane which dissolves in water.

Conventional(ly)—based on the particular meaning known at the time this patent application is drafted and/or interpreted.

Environment—liquid, gel, semi-solid, or solid

Gel—A gel is a type of semi-solid composition in which liquid molecules are dispersed within a solid medium. Gels range in texture from being less viscous, and hence more pliable, to being more viscous, and hence less pliable.

Any and all disclosure herein can apply to all of the disclosed embodiments.

Although this invention has been shown and described with respect to detailed embodiments, those skilled in the art will recognize and understand that various changes in the form and detail may be made without departing from the spirit and scope of the claimed invention.

What is claimed is:

1. A method of creating a colorful environment comprising the following steps:
   a. adding at least one first color composition to at least one of a liquid, gel, semi-solid, or solid, the at least one first color composition comprising a carbonate and/or a bicarbonate of sodium, an acid, lactose, and at least one first colored dye;
   b. dissolving, in whole or in part, the at least one first color composition in the at least one of a liquid, gel, semi-solid, or solid to create a colorful environment in the at least one of a liquid, gel, semi-solid or solid;
   c. determining, during or after the dissolving step of the at least one first color composition, whether the environment has a desired intensity and/or hue of color;
   d. adding at least one additional color composition to the at least one of a liquid, gel, semi-solid, or solid, if it is determined that the environment does not have the desired intensity and/or hue of color, the at least one additional color composition having the at least one first colored dye and/or at least one other colored dye;
   e. dissolving, in whole or in part, the at least one additional color composition in the at least one of a liquid, gel, semi-solid or solid to create a colorful environment in the at least one of a liquid, gel, semi-solid or solid, if the at least one additional color composition is added;
   f. determining, during or after the dissolving step of the at least one additional color composition, in the event step e. occurs, whether the environment has a desired intensity and/or hue of color; and
   g. repeating steps d. through f. if it is determined that the environment does not have the desired intensity and/or hue of color.

2. The method of claim 1, further comprising the following steps:
   h. adding at least one second color composition to at least one of a liquid, gel, semi-solid, or solid, the at least one second color composition comprising a carbonate and/or a bicarbonate of sodium, an acid, lactose, and at least one second colored dye;
   i. dissolving, in whole or in part, the at least one second color composition in the at least one of a liquid, gel, semi-solid, or solid to create a colorful environment in the at least one of a liquid, gel, semi-solid or solid;
   j. determining, during or after step i., whether the environment has a desired intensity and/or hue of color;
   k. adding at least one other additional color composition to the at least one of a liquid, gel, semi-solid, solid, if it is determined that the environment does not have the desired intensity and/or hue of color, the at least one other additional color composition having the at least one second colored dye and/or at least one other colored dye;

l. dissolving, in whole or in part, the at least one other additional color composition in the at least one of a liquid, gel, semi-solid or solid to create a colorful environment in the at least one of a liquid, gel, semi-solid or solid, if the at least one other additional color composition is added;

m. determining, during or after the dissolving step of the at least one other additional color composition, whether the environment has a desired intensity and/or hue of color, in the event step l. occurs; and n. repeating steps k. through m. if it is determined that the environment does not have the desired intensity and/or hue of color.

3. The method of claim 2, wherein the at least one additional color composition comprises a carbonate and/or a bicarbonate of sodium, an acid, and lactose; the at least one other additional color composition comprises a carbonate and/or a bicarbonate of sodium, an add, and lactose; and in each color composition the acid is citric acid and the ratio of the carbonate and/or the bicarbonate of sodium to citric acid is about 2 to about 1.

4. The method of claim 3, further comprising an additional step prior to adding the at least one first color composition to the at least one of a liquid, gel, semi-solid, or solid, the additional step comprising forming the at least one first color composition into a powder, tablet, bath bomb or bath bead prior to adding it to the at least one of a liquid, gel, semi-solid, or solid.

5. The method of claim 4, further comprising the additional step of forming each color composition into a powder, tablet, bath bomb or bath bead prior to adding it to the at least one of a liquid, gel, semi-solid, or solid.

6. The method of claim 4, wherein the additional step forms the at least one first color composition into a powder, and further comprising another additional step of shaking the powder out of its container prior to the step of adding it to the at least one of a liquid, gel, semi-solid, or solid.

7. The method of claim 5, further comprising an additional step prior to forming each color composition into a powder, tablet, bath bomb or bath bead, the additional step comprising formulating at least one of each color composition together with at least one of the following cocoa butter, avocado oil, sunflower oil, flowers, flower buds, tea leaves, lavender, lavender buds, roses, rhea butter, glitter, flower petals, skin conditioning oils, cleansers, skin-conditioning plant oils, essential oils, mineral oils, aroma therapy oils, oatmeal, milk, honey, fragrance, perfumes, Epsom salt, sea salt and/or soap.

8. The method of claim 1, wherein the at least one first color composition comprises:
   sodium carbonate in a range of from about 30 to about 45%,
   sodium bicarbonate in a range of from about 20 to about 35%,
   citric acid in a range of from about 15 to about 35%,
   lactose in a range of from about 5 to about 25%, and
   dye in a range of from about 0.5 to about 3%; and
   wherein water is an ingredient of the at least one of a liquid water, gel, semi-solid, or solid.

9. The method of claim 8, further comprising the following steps:
   h. adding at least one second color composition to at least one of a liquid, gel, semi-solid, or solid, the at least one second color composition comprising at least one second colored dye;
   i. dissolving, in whole or in part, the at least one second color composition in the at least one of a liquid, gel, semi-solid, or solid to create a colorful environment in the at least one of a liquid, gel, semi-solid or solid;
   j. determining, during or after the dissolving step of the at least one second color composition, whether the environment has a desired intensity and/or hue of color;
   k. adding at least one other additional color composition to the at least one of a liquid, gel, semi-solid, solid, if it is determined that the environment does not have the desired intensity and/or hue of color, the at least one other additional color composition having the at least one second colored dye and/or at least one other colored dye;
   l. dissolving, in whole or in part, the at least one other additional color composition in the at least one of a liquid, gel, semi-solid or solid to create a colorful environment in the at least one of a liquid, gel, semi-solid or solid, if the at least one other additional color composition is added;
   m. determining, during or after the dissolving step of the at least one other additional color composition, whether the environment has a desired intensity and/or hue of color, if step l. occurs; and
   n. repeating steps k. through m. if it is determined that the environment does not have the desired intensity and/or hue of color;
   and
   wherein the composition of the at least one additional color composition, the at least one second color composition, and the at least one other additional color composition comprises:
   sodium carbonate in a range of from about 30 to about 45%,
   sodium bicarbonate in a range of from about 20 to about 35%,
   citric acid in a range of from about 15 to about 35%,
   lactose in a range of from about 5 to about 25%, and
   dye in a range of from about 0.5 to about 3%; and
   about 0.1 to about 5% of at least one of the following: cocoa butter, avocado oil, sunflower oil, polyethylene glycol, flowers, flower buds, tea leaves, lavender, lavender buds, roses, rhea butter, gutter, flower petals, skin conditioning oils, cleansers, skin-conditioning plant oils, essential oils, mineral oils, aroma therapy oils, oatmeal, milk, honey, fragrance, perfumes, Epsom salt, sea salt and/or soap.

10. A color composition comprising:
   a composition comprising the following formula:
   sodium carbonate in a range of from about 30 to about 45%,
   sodium bicarbonate in a range of from about 20 to about 35%,
   citric acid in a range of from about 15 to about 35%,
   lactose in a range of from about 5 to about 25%, and
   dye in a range of from about 0.5 to about 3%; and
   about 0.1 to about 5% of at least one of the following: cocoa butter, avocado oil, sunflower oil, polyethylene glycol, flowers, flower buds, tea leaves, lavender, lavender buds, roses, Shea butter, glitter, flower petals, skin conditioning oils, cleansers, skin-conditioning plant oils, essential oils, mineral oils, aroma therapy oils, oatmeal, milk, honey, fragrance, perfumes, Epsom salt, sea salt and/or soap.

11. The color composition of claim 10, wherein the composition is in the form of a powder, tablet, bath bomb or bath bead.

12. The color composition of claim 11, further comprising at least one other color composition comprising the following formula:
sodium carbonate in a range of from about 36 to about 41%,
sodium bicarbonate in a range of from about 23 to about 25%,
citric acid in a range of from about 18 to about 25%,
lactose in a range of from about 10 to about 12%, and
another dye in a range of from about 0.5 to about 2%; and
wherein the at least one other color composition is in the form of a powder, tablet, bath bomb or bath bead.

13. A color kit comprising:
at least one color composition comprising the following formula:
sodium carbonate in a range of from about 30 to about 45%,
sodium bicarbonate in a range of from about 20 to about 35%,
citric acid in a range of from about 15 to about 35%,
lactose in a range of from about 5 to about 25%, and
at least one dye in a range of from about 0.5 to about 3%; and
about 0.1 to about 5% of at least one of the following:
cocoa butter, avocado oil, sunflower oil, polyethylene glycol, flowers, flower buds, tea leaves, lavender, lavender buds, roses, shea butter, glitter, flower petals, skin conditioning oils, cleansers, skin-conditioning plant oils, essential oils, mineral oils, aroma therapy oils, oatmeal, milk, honey, fragrance, perfumes, and/or soap; and
bath salts.

14. The color kit of claim 13, further comprising at least one other color composition comprising the following formula:
sodium carbonate in a range of from about 36 to about 41%,
sodium bicarbonate in a range of from about 23 to about 25%,
citric acid in a range of from about 18 to about 25%,
lactose in a range of from about 10 to about 12%, and
another dye in a range of from about 0.5 to about 2%.

15. The color kit of claim 14, wherein the at least one color composition and the at least one other color composition are in the form of a powder, tablet, bath bomb or bath bead.

16. The color kit of claim 14, wherein at least one of the at least one color composition and the at least one other color composition are in the form of a powder and the powder is in its own container within the kit.

17. The color kit of claim 13, further comprising a color wheel.

18. The color kit of claim 13, further comprising at least one of a paint brush, ice cube tray, egg-dipping container, egg container, and/or dropper.

19. The color kit of claim 13, further comprising plain paper and/or pre-printed paper.

20. The color kit of claim 13, further comprising a container for at least one of a liquid, gel, semi-solid, or solid.

* * * * *